US008568591B2

(12) United States Patent
Knoop (10) Patent No.: US 8,568,591 B2
(45) Date of Patent: Oct. 29, 2013

(54) SYSTEM AND METHOD FOR THERMOPHILIC ANAEROBIC DIGESTER PROCESS (76) Inventor: Robert Knoop, Lake Oswego, OR (US)

( * ) Notice: Subject to any disclaimer, the term of this patent is extended or adjusted under 35 U.S.C. 154(b) by 0 days.

(21) Appl. No.: 13/598,188

(22) Filed: Aug. 29, 2012

(65) Prior Publication Data
US 2013/0015110 A1 Jan. 17, 2013

Related U.S. Application Data (62) Division of application No. 12/581,527, filed on Oct. 19, 2009, now abandoned.

(60) Provisional application No. 61/106,836, filed on Oct. 20, 2008.

(51) Int. Cl.
C02F 3/28 (2006.01)

(52) U.S. Cl.
USPC ........... 210/603; 210/612; 210/631; 210/173; 210/175; 210/259

(58) Field of Classification Search
USPC ................ 210/603, 612, 613, 631, 173, 175, 210/198.1, 252, 259
See application file for complete search history.

(56) References Cited

U.S. PATENT DOCUMENTS

| | | | | | |
|---|---|---|---|---|---|
| 3,658,032 | A | * | 4/1972 | Kohler et al. | 118/725 |
| 3,981,800 | A | * | 9/1976 | Ort | 210/603 |
| 4,710,301 | A | * | 12/1987 | Geuens | 210/605 |
| 5,110,459 | A | * | 5/1992 | Baxter | 210/143 |
| 5,290,450 | A | * | 3/1994 | Kobayashi | 210/603 |
| 6,013,183 | A | * | 1/2000 | Stephenson et al. | 210/606 |
| 6,015,496 | A | * | 1/2000 | Khudenko | 210/603 |
| 6,569,335 | B1 | * | 5/2003 | Johnson | 210/614 |
| 6,790,359 | B2 | * | 9/2004 | Miller, III | 210/603 |
| 7,452,466 | B2 | * | 11/2008 | Binning et al. | 210/603 |
| 7,485,230 | B2 | * | 2/2009 | Magner et al. | 210/603 |
| 2006/0169637 | A1 | * | 8/2006 | Yamaguchi et al. | 210/607 |
| 2008/0223783 | A1 | * | 9/2008 | Sutton | 210/621 |

* cited by examiner

Primary Examiner — Fred Prince
(74) Attorney, Agent, or Firm — Paul Davis; Mintz Levin (57) ABSTRACT A new approach is proposed that contemplates systems and methods to support an environmentally-friendly, "green" thermophilic anaerobic digestion system. The system includes a thermophilic anaerobic digester as well as various independent modular anaerobic units to generate bio-methane from certain organic energy sources, including but not limited to, among other things, green municipal waste, restaurant and organic waste and effluents from industries such as breweries, grocery stores, food processing plants, granaries, wineries, pulp and paper mills, ethanol and biodiesel plants, fat and animal rendering, agricultural field crops, organic sludge accumulation within lagoons and waterways, marine organic matter and animal manure.

23 Claims, 4 Drawing Sheets

SYSTEM AND METHOD FOR THERMOPHILIC ANAEROBIC DIGESTER PROCESS

RELATED APPLICATIONS

This application is a divisional of U.S. application Ser. No. 12/581,527 filed Oct. 19, 2009 now abandoned, which claims the benefit of U.S. Application 61/106,836, filed Oct. 20, 2008, all of which applications are fully incorporated herein by reference.

BACKGROUND

The primary anaerobic digester processes on the market, that are available for industry/agriculture/municipal waste treatment and environmental remediation, include digesters which are either in ground or above ground. In addition, they operate generally at the psychrophilic or mesophilic temperature ranges; however, there are some thermophilic units in operation. The psychrophilic units operate normally at a temperature of 18° C. (65° F.) and the mesophilic units at a temperature range of 35° C. to 40.5° C. (95° F. to 105° F.). There are many variations with these designed anaerobic systems, and each has certain advantages. Detailed below are general descriptions of the three major classes of digester with a further explanation as to some of their critical limitations.

The least expensive digester is an in ground system, such as a lagoon, which is generally an excavated shallow basin with a very large surface area. The sidewalls can be earthen and may include flexible membrane covers. There is generally no agitation in these units and most operate at ambient temperature, i.e.—psychrophilic. In-ground systems (i.e. lagoons) have certain intrinsic problems such as dilution of the process from either groundwater beneath the lagoon or rainwater from the sides or top. Rainwater and snow/ice that accumulates on the flexible membrane cover will depress the cover in certain areas and cause the biogas to collect in pockets. Unintended water within the process dilutes the organic matter, and disrupts the digester temperatures within the unit, affecting the performance and efficiency. High winds and UV radiation also cause problems, damaging the flexible covering. Given the geometry of these lagoons, which are relatively shallow with a large surface area, evaporation combined with the lack of uniform agitation, causes a significant and inevitable accumulation of inorganic and heavy organic matter. Generally, these systems are shut down annually for over a month to allow for solids removal and subsequent restart of the process. Maintaining proper operating temperature is recognized as a technical problem endemic to these units. This lack of temperature and exposure time results in a marginal and unpredictable pathogen kill. Most if not all in ground lagoons require a secondary lagoon in which the processed feedstock needs up to an additional 180 days to complete the process to meet nutrient management requirements. Additional aerobic composting in windrows may also be required.

Some in-ground units may incorporate concrete channels, which are laid out in either a long linear fashion or are in a U-shaped configuration. These units typically have concrete walls with concrete lids (or flexible membrane covers) and are built into the ground to retain process heat. These units are generally mesophilic. Heating is typically provided by heating coils or pipes installed either under the digester concrete channel or in the central concrete wall, which separates the two adjacent channels of the U-shaped configuration. In all cases, the heat is transferred by a combination of conduction and convection through the wall and then across the full width of the plug flow within the channel. The hydraulic residence time (HRT), which is the duration for which material to be digested will remain in the digester, ranges from 18 to 28 days. This long duration time necessitates a long digester chamber length and/or a slow throughput which in turn introduces mechanical difficulty providing proper and uniform agitation along the full length of the digester. As a result, without consistent agitation, heating is not uniform and hot and cold areas develop along the length of the digester. Negatively impacting digester performance as measured by throughput, volatile solids destruction, methane gas production and pathogen kill rates. In addition, the lack of uniform agitation along the length of the digester results in the accumulation of inorganic and heavy organic materials that have been introduced into the digester. It should be noted that although the heavy organic matter can be broken down within the digester, any overlay of inorganic matter above the heavy organic matter (such as sand) may isolate the organic matter from the anaerobes. Over time, and generally within one year, the digester needs to be shut down to remove this accumulation of material. This is necessary as the digester's operating volume slowly decreases, due to this buildup, which, if left unattended, will ultimately blind off and restrict the flow through the digester. When this type of digester is shut down, cleaned out and restarted, up to a month of operating time is generally lost.

The above ground, anaerobic digester systems are normally made of poured in place concrete or steel construction materials and insulated as required. These materials are sturdy and water tight thus eliminating many of the intrinsic problems associated with lagoons such as water and wind. However, heat management is very critical to the efficient performance of this type digester. Generally, these vessels are cylindrical in nature and are approximately 12 m (40 ft.) in diameter, and 12 m to 15.25 m (40 to 50 ft.) in height with a vessel volume of 2500 m$^3$ (88,290 ft$^3$) and greater. In the case of the mesophilic units researched, hot water piping is usually located around the interior circumference of the vessel used as an aid in maintaining the optimal operating temperature. An efficient digester should have uniform temperatures throughout the vessel, within a tight tolerance of +/−1.2° C. or 2 ° F. However, convective and conductive heat transfer alone do not provide for homogenous heating throughout a vessel of this size. Therefore, in order to move heat to the center of the vessel mass, agitation is required. This is normally provided by a top or side mounted unit with blades and sufficient energy to occasionally roll over the vessel contents. Top mounted agitators are usually located off centre with horizontal paddles near the top and bottom of the shaft. These agitators attempt to distribute the heat and achieve more uniform temperatures within the digester; however the flow related process requirements for the digester are compromised. The fresh feedstock is mixed in with the older feedstock very quickly, negatively impacting volatile solids destruction, methane gas production, yield, and pathogen kill.

In addition to these above ground anaerobic mesophilic digester systems, there are similar units (far fewer) operating at the thermophilic temperature range of 44° C. to 70° C. (110° F. to 160° F.). Heat management is even more critical to the efficient performance of this type of digester. Generally, as in the case of the mesophilic type of digester described above, these thermophilic units have similar dimensions, capacities and heating/agitation systems. Due to the higher operating temperature of these other thermophilic units, the quantity and resulting surface area of the hot water piping located around the interior circumference of the vessel is increased. To attain the tight temperature tolerances required for digester efficiency, external heat exchangers may be required as convection and conduction alone may not suffice. The temperature of the hot water must also be increased to accelerate the heat transfer rate. This increased ΔT then leads to localized caking and subsequent insulation of the heating pipes. The intensity or level of agitation must also be increased to aid in the heat transfer and the required tight temperature control demanded by the thermophilic process. This increased agitation has the side effect of causing the methane producing bacteria to become dormant and produce less gas. The flows of the contents through the vessel as a result of the increased agitation will also short circuit the passage of the feedstock through the unit, compromising pathogen kill certainty. This short circuit condition does not permit the feedstock to be held at the higher system operating temperatures for the length of time mandated to achieve pathogen kill levels.

Consequently, many of the systems in use as described above require a secondary vessel to finish the digestion process, adding to the Hydraulic Retention Time (HRT). In the event that a secondary anaerobic digester is not installed, the discharge from these digesters can be dewatered and transferred to storage areas for wind rowing. Wind rowing, which is aerobic digestion, is used to complete the overall digestion process to meet nutrient management requirements. Each incremental process step adds significantly to the overall digestion time duration, as well as project cost, operational cost, and overall area requirements. If these additional process steps are not included, the digester performance (as measured by methane gas production, quality, volatile solids destruction, pathogen kill, hydraulic residence time and the final digestate chemical inertness), will be measurably less than the results from the digester technology as covered by this patent description.

The foregoing examples of the related art and limitations related therewith are intended to be illustrative and not exclusive. Other limitations of the related art will become apparent upon a reading of the specification and a study of the drawings.

DETAILED DESCRIPTION OF EMBODIMENTS

The approach is illustrated by way of example and not by way of limitation in the figures of the accompanying drawings in which like references indicate similar elements. It should be noted that references to "an" or "one" or "some" embodiment(s) in this disclosure are not necessarily to the same embodiment, and such references mean at least one.

A new approach is proposed that contemplates systems and methods to support an environmentally-friendly, "green" thermophilic anaerobic digestion system. The system includes a thermophilic anaerobic digester as well as various independent modular anaerobic units to generate bio-methane from certain organic energy sources, including but not limited to, among other things, green municipal waste, restaurant and organic waste and effluents from industries such as breweries, grocery stores, food processing plants, granaries, wineries, pulp and paper mills, ethanol and biodiesel plants, fat and animal rendering, agricultural field crops, organic sludge accumulation within lagoons and waterways, marine organic matter and animal manure. The thermophilic anaerobic digestion system is uniquely designed to handle many types of industrial and municipal organic waste streams simultaneously or separately. It also offers advantages over current digester systems, including its more modular and inter-changeable design (which expedites project construction), faster throughput digestion, smaller space requirements, higher gas production, superior pathogen and BOD/COD destruction rates, better odor capture and control, higher flexibility of feedstock usage.

The thermophilic anaerobic digestion system is primarily aimed at the effect of inorganic matter on system. An anaerobic digester modular unit has been designed for experimental purposes and information gained from the design, installation, testing, operational monitoring and recording of the unit has been accumulated, verified and incorporated herein. Among those operational findings it is discovered that, regardless of the separating pretreatment used, inorganics, if originally in the feedstock cannot be completely removed. Thus one of the novel characteristics of this system is its self-cleaning attribute, which enables the system to continuously operate using a contaminated feedstock. Additionally, other design attributes provide for ease of operation. The presence of wood shavings as a bedding material, found frequently in agricultural manure, does at times plug associated process pipelines of diameters 3 inches and smaller. This is remedied by installation of water lines where outlets are attached in strategic locations with valves for back flushing for both above ground and in ground lines.

Figure 1:
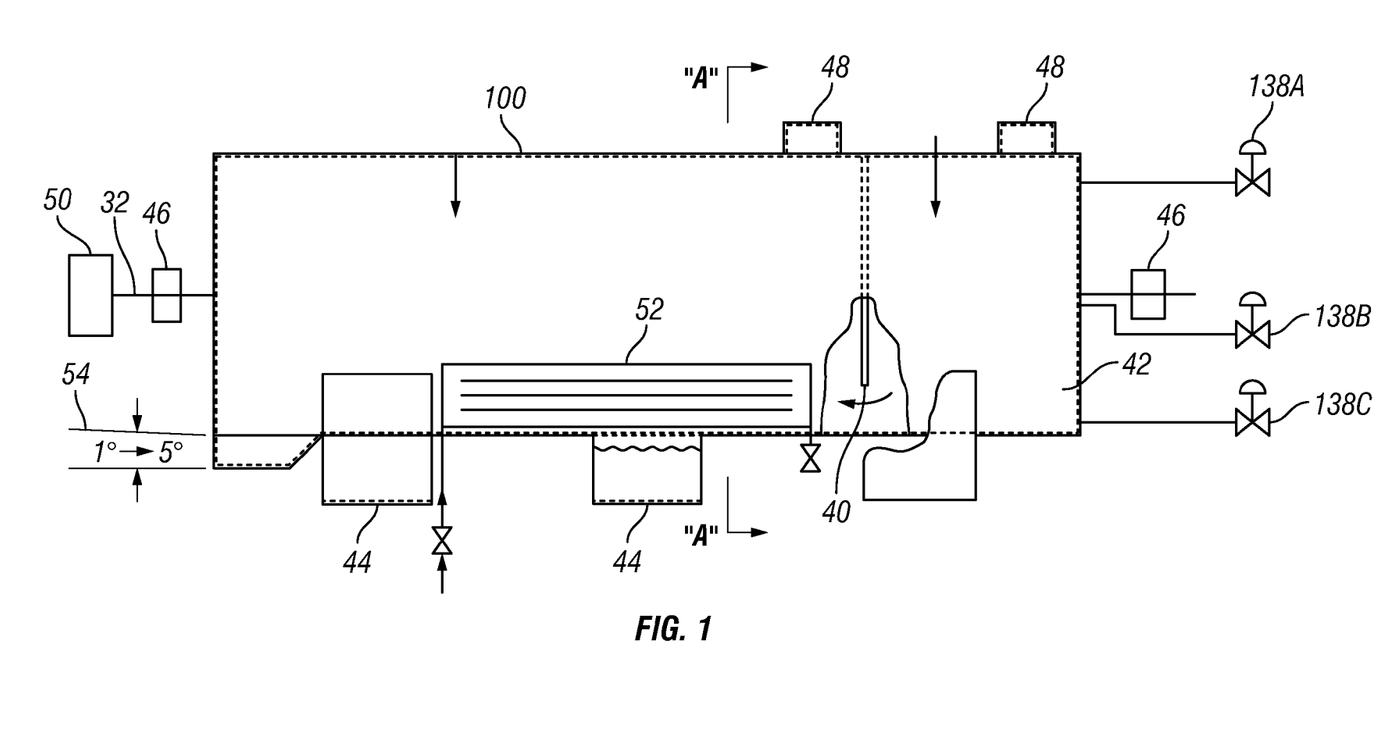
FIG. 1 depicts a side view of an example of a thermophilic anaerobic digester.
Figure 2:
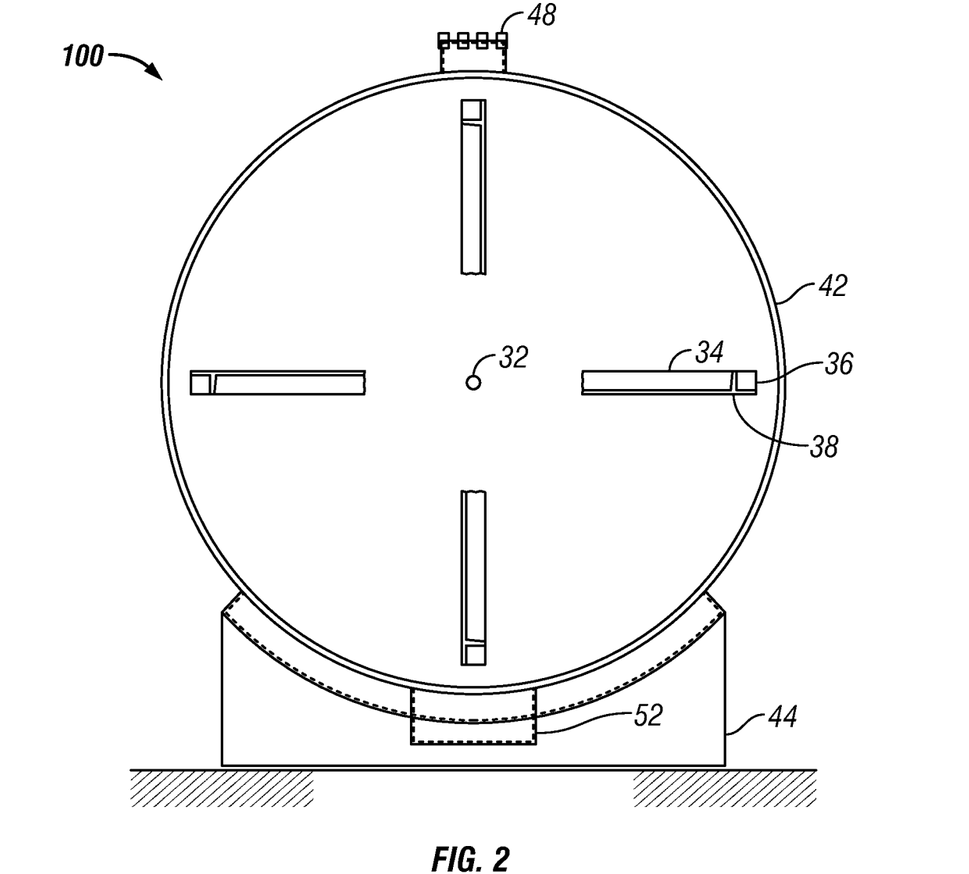
FIG. 2 depicts a cross sectional view of the example of the digester along section line A-A shown in FIG. 1.

FIG. 1 depicts a side view of an example of a thermophilic anaerobic digester 100 utilized by the anaerobic digestion system. Although the diagrams depict components as functionally separate, such depiction is merely for illustrative purposes. It will be apparent that the components portrayed in this figure can be arbitrarily combined or divided into components. FIG. 2 depicts a cross sectional view of the example of the digester along section line A-A shown in FIG. 1.

The thermophilic anaerobic digester 100 depicted in FIGS. 1 and 2 includes a cylindrical digester vessel (tank) 42 mounted horizontally above ground and optimally sloped between 1° to 5° off horizontal, although other angles will function but at reduced efficiency. The vessel 42 can be fabricated from carbon steel and when closed off is sealed to oxygen from the atmosphere providing for the anaerobic environment. The vessel 42 is supported by vessel saddle supports 44. These supports 44 raise the tank off the ground there by permitting the installation of digester heating device 52 and related equipment insulating layer 128. This vessel design was selected to maximize hydraulic plug flow characteristics and integrity. Plug flow exists when each batch of new feedstock travels the length of the digester vessel 42 without intimate mixing with the feedstock batches added either beforehand or after that particular batch. The slope of the vessel 42 causes the heavier material, which tends to settle to the bottom of the cylindrical vessel 42, and has a higher concentration of inorganics to travel with the plug flow from the in-feed end to the discharge end. The vessel design/orientation also facilitates the installation of digester vessel internal baffle(s) 40 and variable decanting at the discharge of the thermophilic anaerobic digester 100. These internal baffles 40 ensure that the plug flow traveling through the thermophilic anaerobic digester 100 must follow a predetermined path which intern ensures no intermixing. These process attributes optimize Hydraulic Retention Time, Solids Retention Time, upstream inoculation, downstream solids separation and pathogen kill.

In some embodiments, the dimensions of the digester vessel 42 provide for a modular system that can be transported by rail or road to the installation site. This transportation flexibility allows the thermophilic anaerobic digester 100 depicted in FIGS. 1 and 2 to be used for a variety of process applications such as the one shown in FIG. 4. In addition, the digester vessel 42 can be fabricated off-site more cost effectively in fabrication shops thereby enhancing quality, production schedules and unit costs. Also, this modular concept (which permits full size digester vessel 42 shipping to site) also permits the cost effective addition of incremental modules such as thermophilic anaerobic digester 100, which in turn allows allocation of different feedstocks to different units on the same site. The modularity and limited foot print permit installations at existing sites which have been judged to be land locked and too small for an anaerobic digester installation using other technologies.

One of the key distinctions of the thermophilic anaerobic digester 100 depicted in FIGS. 1 and 2 that sets it aside from these other thermophilic units currently available is the totally different vessel dimensions, modularity of capacity additions, heating and contents agitation as well as the pretreatment feedstock conditioning. The only feature they share is the operating temperature. Since the vessel geometry of a length to diameter ratio is set to 3:1 to 5:1 to optimize thermophile and feedstock mixing through the use of a longitudinal agitation arrangement (co-axial with the horizontal digester vessel 42), there are no "unmixed" areas of the thermophilic anaerobic digester 100. This optimized mixing configuration, combined with the sloping vessel configuration, moves heavy organic and inorganic materials (which accumulate in the rounded "belly" of the digester 100) and slowly propels this accumulated material to the discharge end. Consequently, no accumulations build up and therefore, shutdowns due to plugging or loss of operating capacity do not occur. Therefore the thermophilic anaerobic digester 100 is a self-cleaning unit and very tolerant of a contaminated feedstock. These unique features of the thermophilic anaerobic digester 100 and process allow the digestion of less uniformly sized feedstock. There are no negative implications to feeding the anaerobic digester 100 with feedstock organic matter up to 2 cm (0.75 in) in diameter.

In some embodiments, the digester heating system 52 and 170 are external to the digester vessel 42. The vessel 42 is fabricated with a water jacket along the underbelly of the vessel 42, utilizing convection and conduction heat transfer for homogenous heating throughout the vessel 42. There is no potential for contamination of the vessel contents due to leakage of any re-circulated glycol or other heating solutions.

In some embodiments, the thermophilic anaerobic digester 100 depicted in FIGS. 1 and 2 requires a Hydraulic Retention Time (HRT) of 3 to 7 days as compared to an average of 16 to 80 days for psychrophilic, mesophilic or other forms of thermophilic anaerobic digesters. Completion of digestion is achieved when the percentage volatile solids destruction plateaus and longer residence time does not significantly increase the level of volatile solids destruction. Other digesters may define HRT based upon this criterion or simply based upon digester residence time. This latter approach doesn't incorporate any final Volatile solids destruction targets. Consequently, gas production may not be optimized. If the process must comply with government nutrient management criteria (application of digestate to open land) the volatile solids destruction levels are too low and ammonia content may be excessive. In such cases additional digestion process steps may be required.

In some embodiments, the thermophilic anaerobic digester 100 depicted in FIGS. 1 and 2 can achieve volatile solids destruction (VSD) levels of 50% to 65% for animal waste. The best VSD's achieved by these other technologies will be up to 53%, with averages in the low to mid 40's. The FDA has defined that a certain temperature/duration is required in order to achieve effective pathogen kill. Although some current digester technologies are operated for more than the extended time periods required by the appropriate government agency, their low temperatures are insufficient to achieve the pathogen kill required to achieve compliance with governmental regulatory mandates concerning nutrient management. In fact, all mesophilic systems need to sanitize certain feedstocks (or the digestate) for 1 hr. at 70° C. (160° F.) in order to achieve compliance. One of the advantages of the thermophilic anaerobic digester 100 and its thermophilic process is that most pathogens are killed during the initial 24 hours of operation. Current regulations (both European and North American) state that 20 hours at 55° C. (130° F.) is sufficient. Subsequently, after a normal HRT duration, the pathogen kill using the thermophilic anaerobic digester 100 is 99.999%.

Solids Retention Time (SRT) is the most significant variable, which indicates the amount of solids conversion (Volatile Solids (VS)) to biogas and liquid in the digestion process (i.e., the quantity of VS destroyed each day). As stated above, the SRT value represents the total amount of conversion from volatile solids to biogas within the digestion process and therefore represents the overall efficiency of the digestion process in converting volatile solids to biogas. The equation below defines how SRT can be calculated:

$$SRT = \frac{(V)*(Cd)}{(Qw)*(Cw)}$$

V=Daily Infeed Volume into the Digester Process
Cd=Solids Concentration of the Infeed
Qw=Daily Quantity of VS destroyed, (COD infeed−COD discharge)
where COD means chemical oxygen demand.
Cw=Solids Concentration of the Waste Effluent (discharge from the digester process)

Volatile Solids destroyed is related to the reduction in Chemical Oxygen Demand. Initial destruction rates are relatively fast but, at some point in the digestion process, the rate of VS destruction will drop dramatically, as indicated by a decrease in biogas production. At that point, it is concluded that there will be limited benefit in retaining the material with in the digester process any longer and therefore, the material is discharged. The total volatile solids destruction claimed is therefore based only on the destruction achieved while at the initial faster rates. Therefore the Chemical Oxygen Demand of the thermophilic anaerobic digester 100 depicted in FIGS. 1 and 2 is equal to the net difference in COD between the digester influent and effluent resulting from the volatile solids destruct rate over the period where that volatile solids destruct rate was fastest.

A measure of the success of biomass retention is the SRT/HRT (solids retention time/hydraulic retention time) ratio. The thermophilic anaerobic digester 100 depicted in FIGS. 1 and 2 is adjustable in order to achieve a SRT/HRT ratio that optimizes the volatile destruction and the corresponding gas production. In some embodiments, the SRT/HRT ratio of the thermophilic anaerobic digester 100 depicted in FIGS. 1 and 2 is in excess of 1. A major influence is the much shorter HRT claimed by the system process. Current technology digesters have long HRT values. The volatile solids destruction in the generic systems is lower than in the thermophilic anaerobic digester 100 depicted in FIGS. 1 and 2 due to the non-optimized mixing, heating and flow characteristics of material as it works its way through the unit. In other technologies, where the SRT is low (fast) it does not allow enough time for the bacteria to grow and replace the lost bacteria discharged with the digestate and if the rate of loss exceeds the rate of growth, "wash out" occurs. If this critical SRT time period is breached, the digester performance falls off dramatically and substantial time is required to repopulate the bacteria and restart the process.

Figure 4:
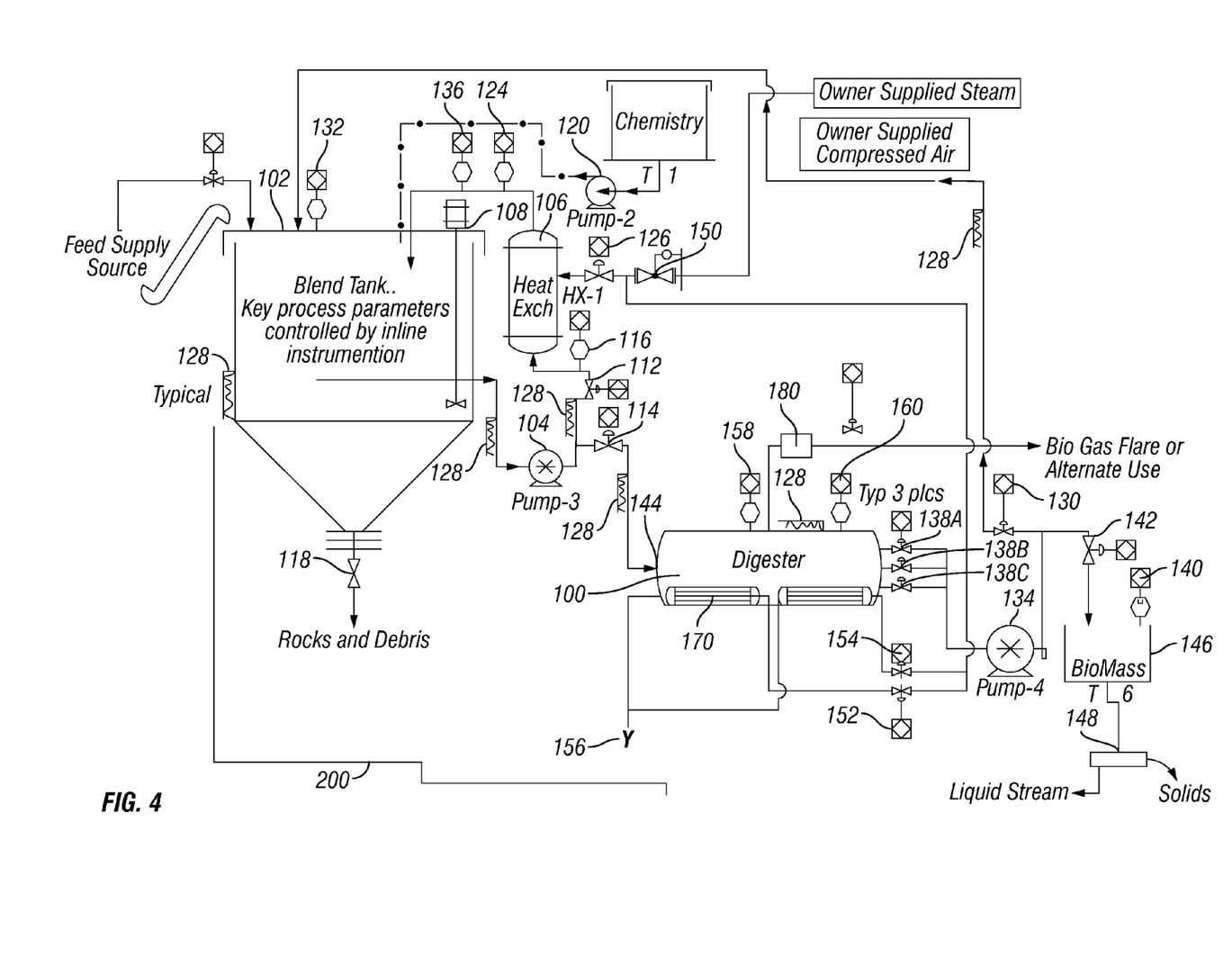
FIG. 4 depicts an example of a process flow diagram of an anaerobic digestion system utilizing the thermophilic anaerobic digester shown in FIGS. 1-2.

In some embodiments, the thermophilic anaerobic digester 100 depicted in FIGS. 1 and 2 has a high SRT/HRT ratio while avoiding the washout condition. This unit can claim this process efficiency (high ratio) for two main reasons:

First: the thermophilic anaerobic digester 100 inoculates incoming fresh feedstock with a recirculated volume from the thermophilic anaerobic digester 100 by transferring digestate from the end of the unit back into upstream blend tank 102 through digester infeed valve 130 in the anaerobic digestion system depicted in FIG. 4. This is done upstream and before the new feedstock enters the thermophilic anaerobic digester 100. Without increasing the size of the digester 100, the exposure time between the bacteria and the feedstock has been extended. The thermophilic anaerobic digester 100 achieves a larger effective SRT value by extending the exposure time of the feedstock to the inoculants by use of blend tank 102 (upstream of the digester 100 itself). This intermixing of feedstock and bacteria occurs without increasing the digester vessel volume and consequently, the HRT value is not increased. Maintaining a longer SRT and a higher SRT/HRT ratio avoids the potential of a bacteria "washout" condition.

Second: the variable decanting capability at the discharge of the digester enables the anaerobic digestion system 200 depicted in FIG. 4 to draw the majority of the effluent from the middle valve 138B, where the solids resulting from incomplete digestion are of a lower concentration. The majority of the solids accumulate at the top and bottom of the digester 100, thus allowing the solids a longer residence time inside the digester vessel 42. The net benefit is an effectively longer SRT without change to HRT and therefore a higher overall SRT/HRT ratio.

In some embodiments, the thermophilic anaerobic digester 100 depicted in FIGS. 1 and 2 avoids buildup of heavy organic and inorganic material at the bottom of the vessel via self-cleaning and agitation. Once moved along the inner circumference and to the top position, the material due to its heavier weight will tend to migrate to the lower segments of the flow. Sloped orientation of the vessel in combination with the agitation gradually propels the heavier organic and inorganic matter to the end (discharge) of the digester 100. This feature enables the thermophilic anaerobic digester 100 to operate effectively with the presence of inorganic matter and eliminating solids build up. This ensures avoidance of digester component or sidewall premature wear, as well as the avoidance of periodic digester shutdown maintenance in order to clear inorganic buildups.

Figure 3:
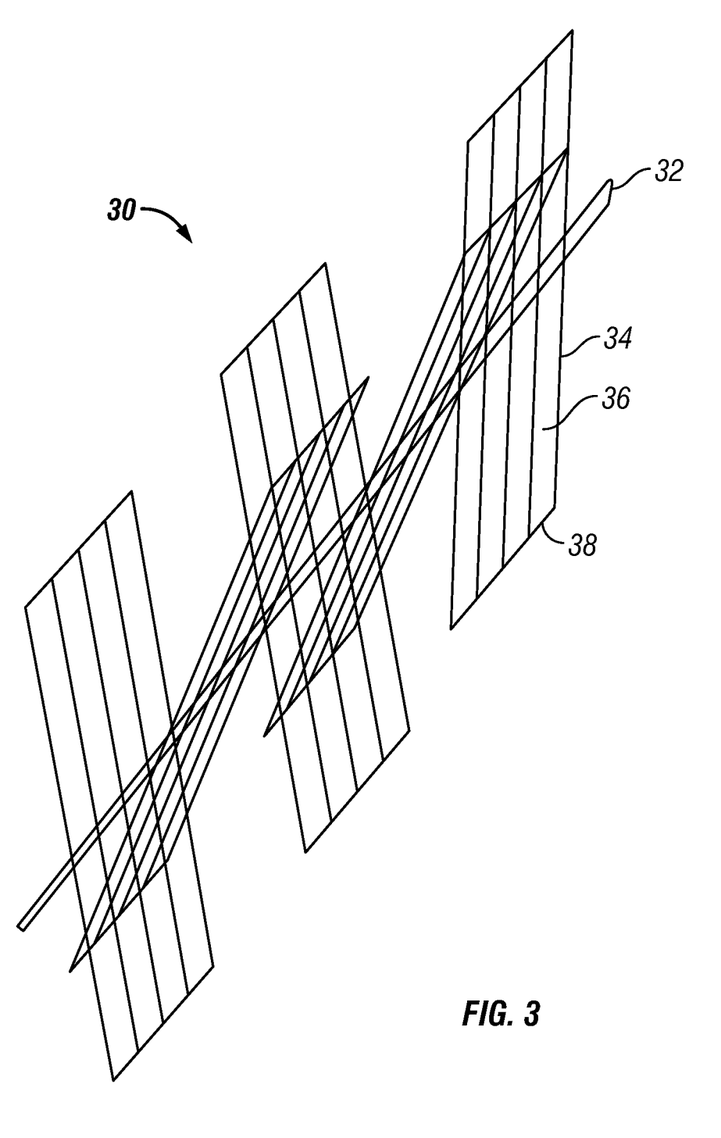
FIG. 3 depicts the structure of an example of an agitator for the thermophilic anaerobic digester shown in FIGS. 1-2.

FIG. 3 depicts the structure of an example of a mechanical agitator 30 used in the thermophilic anaerobic digester 100 shown in FIG. 1-2, where components 34, 36 and 38 of the agitator 30 are located 90 degrees apart on a radial basis to propel inorganic material along the bottom. Agitation is critical in that proper agitation works synergistically within the thermal environment. The internal agitator arrangement runs the full length of the digester 100 unsupported internally and spans the full diameter such that no region exists internally which is not agitated. One of the novelties of the agitator 30 is the flexibility to modify the internal action of the agitator. The agitator 30 can be adjusted to be completely neutral, meaning that the agitation does not move the plug flow along the length of the vessel 42 unless adjusted to do so. It can be modified to have a more directional sweep assisting in moving heavier matter along the bottom of the digester 100. This is done only at the extreme radial end of the agitator near the inner wall. This would not significantly disturb the plug flow integrity.

In some embodiments, each of the agitator components—agitator shaft 32, paddle frame structure 34, paddle plate 36, and localized end-of-paddle sweeps 38—of the agitator 30 depicted in FIG. 3 adopts an adjustable leading edge to cope with contamination, such as the presence of sand in an agricultural feedstock. This inorganic and indigestible matter accumulates at the decanting end of the digester 100 and is removed during the decanting process. The thermophilic anaerobic digester 100 has proven viable as a result of continuous operations during the test period, without shutdowns due to sand build up. Upon shut down, the digester 100 was emptied and the internals were inspected. Residual inorganic matter was of diminutive volumes (of no consequence to the process) and was removed by simple manual labor and wash down.

In some embodiments, the agitator 30 depicted in FIG. 3 turns the material within the plug flow zone into itself by mixing radically away from the central shaft of the agitator 30 out toward the outer vessel circumference. Only rolling digestate movement is achieved with the agitator 30. This design mitigates problematic agitation (too violent). This gentle rolling agitation intimately brings nutrients to the bacteria and vice versa, which minimizes disturbance to the microbes and thus avoiding the condition where the anaerobes become dormant. This unique design feature ensures that the unit is self-cleaning and keeps the feedstock solids from forming a crust at the top of the liquid level within the digester. Any initial crust formation is re-submerged below the surface of the liquid within the digester and rewetted, thereby re-exposing it to the anaerobes.

In some embodiments, the length to diameter ratio geometry of 3:1 to 5:1 of the vessel 42 permits the agitator 30 depicted in FIG. 3 to achieve optimum thermophile and feedstock mixing without excess agitation, which could cause the anaerobes to go dormant. The internal agitator configuration permitted by this vessel geometry achieves multiple objectives. The agitation is gentle and neutral. The longitudinal vanes of components 34, 36 and 38 that run the length of the digester parallel to the vessel central axis of component 32 move the solids along the bottom and are assisted by the slope of the digester 100 and move solids radially and axially based upon end of paddle sweeps 38. This has the combined benefit of moving the nutrients to the anaerobes and the settled heavy solid inorganic material (on digester bottom) to the end of the digester 100. This full diameter and longitudinal gentle agitation also keeps a crust from forming at the liquid interface, which would inhibit gas production and removal from the digester 100. These vanes continuously re-wet the lighter solids. This agitator configuration also reintroduces some of the heavier organic material, which has tended to accumulate along the inside belly of the digester back into intimate contact with the microbes.

In some embodiments, the agitator 30 depicted in FIG. 3 has self-cleaning capability and is able to achieve complete, uniform but non-violent homogenization of the vessel contents. In addition, temperature stratification and localized hot or cold spots are eliminated, thereby increasing digester efficiency. With the addition of internal baffles 40, biological integrity of the plug flow through the digester is enhanced and maintained. These baffles, when combined with the gentle agitation as described above, provide for a plug flow integrity, such that the fresh feedstock progressively degrades into digestate. These baffles also ensure the plug flow integrity of the path through the digester and avoid the mixing of material added mostly recently with that added earlier. No "short-circuiting" can occur.

Note that all agitator wearable parts and accessories (such as pumps, valves, etc.) are external and easy to replace or repair, should such need arises to external agitator bearings 46, ratchet and pawl agitator drive 50 and agitator drive 144. Repairs are expeditious and only a few hours downtime are required. The system is modular and thus the upset of one digester is also not catastrophic.

FIG. 4 depicts an example of a process flow diagram of the anaerobic digestion system 200 utilizing the thermophilic anaerobic digester 100 shown in FIGS. 1 and 2. Primary components are numbered and defined on the side of FIG. 4. Components of the system are a mix of common industrial components such as valves, field sensors, pumps and other related process equipment which process unique equipment specific to this novel invention. All components are required to allow the thermophilic process to operate successfully.

The anaerobic digestion system 200 depicted in FIG. 4 is operable at a slat barn dairy operation where the manure is pumped by chopper pump from the barn pit to the blend tank 102. The blend tank 102 is designed and operated as a multifunctional device. The first function is to remove significant inorganic matter, such as sand, rock and related materials. The second function is to preheat the manure in preparation for the subsequent process steps. The third function is to allow introduction of exterior organic material (EOM) to the process. The blend tank 102 has a conical bottom configured to remove inorganic matter such as sand, pebbles and small rocks. The inorganic matter is then discharged from the anaerobic process through inorganics 118. One significance of the anaerobic digestion system 200 is the substantial removal of inorganic material, with the remainder being removed by further measures discussed below.

The Feedstock

In some embodiments, a feedstock of known low nutritive value (as pertains to commonly held digester nutrients) can be used for the purposes of prototypical testing of the anaerobic digestion system 200 depicted in FIG. 4. The feedstock was dairy manure, sourced from the slat barn collection installation. The bedding initially was hay; but was switched to wood shavings. The wood shavings, due to the lignin content of the wood, do not digest readily. Thus, the wood shavings would water log and accumulate along the bottom of the digester. Recognizing the fact that feed stock such as wood and related products are not "digestible" with technologies such as claimed, verified is the fact that materials such as this presented no problem to the daily operation of the digester. In over continuous operation with this poor quality feedstock, the system proved capable of moving the sand, wood shavings and other settled material along the bottom of the digester for decanting.

In some embodiments, the anaerobic digestion system 200 depicted in FIG. 4 operates with a multiplicity of feedstock materials. For the purpose of pilot testing, the worst case feed was chosen. This feedstock management is crucial to achieving the anaerobic digestion system operating efficiency. The slat barn pilot test site was very inefficient, and presented a worst case scenario for the anaerobic digestion system 200 depicted in FIG. 4. This includes such non-controllable variables as: ground water dilution of the feedstock, inclusion of milk house wash down (with entrained antibiotics) and fluctuations in temperature, nutrient and inorganic parameters, as well as feedstock consistency.

In some embodiments, the anaerobic digestion system 200 depicted in FIG. 4 digests organic matter. The system may not break down the lignin in wood products, but can handle lignin deleted material, if introduced in limited quantities.

The slat barn collection process made impossible to collect fresh manure and transfer to the anaerobic digestion system. The anaerobic digestion system digests the volatile organic compounds (heretofore Volatile Solids or VS), which are normally >80% of the Total Solids (TS), as confirmed by independent lab analysis. VS degrades with time, so fresh manure produces the optimum amount of biogas energy and higher digester efficiency, as measured by solids destruction rates.

Decanted Digestate

Governing bodies and regulatory agencies worldwide recognize the benign (and even beneficial) environmental aspects of the anaerobic digestion system digestate. Therefore, regulations are much less stringent than those applied to the storage and disposal of untreated waste. In some embodiments, the anaerobic digestion system 200 depicted in FIG. 4 discharges liquid digestate to the bio mass tank 146 for processing and storage. The digestate taken from the thermophilic anaerobic digester 100 and transferred through discharge valve 138B can be analyzed through laboratory testing to confirm that there was no significant loss of nutritional value (as represented by nitrogen, phosphorus and potassium levels here to fore NPK) incurred by the digestion process. Subsequent processing of the digestate yields separated solids which proved to be a valuable by-product as a soil amender and field testing with a local greenhouse verified success. The by-product worked exceedingly well and surpassed the greenhouse operator's expectations, as evidenced in single sided testing. Significant increases in crop yield, quality and enhanced flavor were all observed and documented. Note that some sand may accumulate in the bottom of the bio mass tank 146, which requires an annual wash down. This minor maintenance is simple and has no affect on the continuous operation of the anaerobic digestion system.

In some embodiments, the anaerobic digestion system 200 depicted in FIG. 4 stores digestate in one or more of: insulated equipment insulating layer 128, heated heat exchanger 106, blend tank 102, and bio mass tank 146 during digester maintenance, allowing the slurry to remain biologically active. This feature is key to allowing preventative maintenance to be performed without significantly or deleteriously impacting operational stability. Once system repairs are completed the slurry can be pumped back to the digester and the anaerobic digestion process immediately resumed.

The following is a detailed description outlining the attributes of the design of the anaerobic digestion system depicted in FIG. 4, including the upstream pre-treatment equipment and the digester vessel with downstream capabilities.

Pre-treatment

In some embodiments, the anaerobic digestion system 200 depicted in FIG. 4 performs the upstream processes and activities via one or more components of blend tank 102, process pump 104, heat exchanger 106, blend tank agitator 108, recirculation valve 112, digester feed valve 114, consistency measurement sensor 116, inorganic valve 118, ph adjust chemical metering pump 120, blend tank discharge valve 122, temperature sensor 124, temperature control valve 126, equipment insulating layer 128 positioned throughout system 200, digestate infeed valve 130, blend tank level sensor 132 and ph sensor 136, wherein the upstream processes and activities are operational, chemical, biological and occurring prior to the in-feed of the main digester 100. As such, these components are an integral part of the anaerobic process. In addition to recirculating in coming material for heating, chemical addition, and mixing for homogeneity, this process pump 104 can also transfer prepared materials to transfer into the digester 100. The various feedstocks are prepared for digestion by processing the in-feed (raw) material as detailed below. These unit process steps are done at the blend tank 102 and the heat exchanger 106 located in the recirculation loop. The pre-treatment steps are accomplished and controlled within the blend tank 102. Raw material is pumped into the tank 102 or conveyed in, depending on the consistency of the feedstock. If the material is of a low consistency, it will be pumped directly into the tank 102. If it is of a higher consistency, it will be conveyed or pumped into the tank 102 based upon the site conditions. Adjustment of the carbon to nitrogen ratio may be performed at this time through the addition of other feedstocks as discussed below. In the case of a feedstock with the optimal consistency of 2% to 12%, the blend tank 102 and discharge process pump 104 will immediately re-circulate the material through the heating loop and back into the tank. In the event that steam is available as a heating source at the blend tank heat exchanger 106 and for the thermophilic anaerobic digester 100, specifically for the digester heating system 170, a steam pressure regulating valve 150 may be required.

In some embodiments, the anaerobic digestion system 200 depicted in FIG. 4 draws a specific volume of digestate (or that amount required for dilution) from the digester discharge and reintroduces/re-circulates it to the blend tank 102 to inoculate the new feedstock batch through digester discharge valve 1388 and pumped via digester discharge pump 134 back to the blend tank 102. This digestate is at the processing temperature within the digester 100 so this will help to heat up the contents of the blend tank 102. Off site inoculants may also be added as necessary to increase the bacterial viability of the feedstock. Upon addition of these inoculants, the level of agitation is decreased to minimize the "shock" effect on the thermophiles. In combination with the inoculation process, enzymes (which act as digestion catalysts) may be added at this stage of the process. During the chemical addition, the level of agitation in the tank is increased to distribute the chemicals quickly and uniformly by blend tank agitator 108.

In some embodiments, the anaerobic digestion system 200 depicted in FIG. 4 operates within a pH range of 4.0 to 8.5, however the optimal pH range for thermophiles is 7.5 to 8.0 and the optimal pH range for the incoming feedstock is 6.5 to 7.0. Consequently, pre-treatment will have to adjust (if necessary) the pH parameters of the feedstock to within that pH range by chemical injection using pH adjust chemical metering pump 120 and pH sensor 136 located in the recirculation loop. For a non-limiting example, the pH can be adjusted to >6.5. Conditions where pH is outside of this range are tolerable but at dramatically reduced performance levels. Performance is measured by reduction in Biological Oxidation Demand (heretofore BOD), Chemical Oxygen Demand (heretofore COD) and production of Methane gas (heretofore $CH_4$). Methane is collected from the upper levels of the digester vessel 42 through the gas collection domes 48. Most methanogens are neutraphiles meaning that they perform better in a pH range of 6.5 to 7.5. Thus by adjusting the pH to a minimum of 6.5 the feedstock is conditioned to a level of pH that is conducive to good methanogenic activity within the digester.

Throughout this pre-treatment phase, blend tank agitator 108 may aggressively blend and bring about homogeneity of feedstock particle size within the blend tank 102. The blend is generally constructed of carbon steel and is insulated to retain process heat. Additionally, the specifically configured conical section of the blend tank 102 combined with the tangential material flow located at the bottom of the blend tank 102 will remove large solid material greater than ⅝ inch in diameter. This step is required to reduce variations in oversize organic material and optimize hydrolysis. Without doing so, the digester performance will be sub-optimal leading to reduced volatile solids destruction within the digester. In addition, this hydrolysis step must be completed to facilitate the downstream acidification step.

In some embodiments, the anaerobic digestion system 200 depicted in FIG. 4 preheats various feedstocks in the blend tank 102 to the processing temperatures (such as within the thermal operating range of 97° F. to 158° F.) required for thermophilic digestion in the downstream digester 100 using heat exchangers 106 and temperature sensors 124 located in the primary recirculation loop. After the batch has reached the target pH level and required temperature, the system controls the recirculation valve 112 and digester feed valves 114 to pump the contents to the digester 100. If the feedstock is too low in temperature, it will shock the thermophiles in the digester 100, thus negatively affecting the performance of the anaerobic digestion system 200. The temperature of the feedstock must attain the operating temperature of the anaerobic digestion system 200, which can range from 35° C. to 70° C. based upon the anaerobic process selected. The thermophilic anaerobic digester 100 will operate optimally from 44° C. to 70° C.

During acidification stage following the hydrolysis, a new group of bacteria called acetogens become active. These bacteria decompose amino acids into acetic acid and hydrogen, nitrogen and carbon dioxide gases. To do this, they need oxygen, which they obtain from $O_2$ dissolved in the feedstock structure and liquid. While acetogens are anaerobic bacteria, oxygen is not as poisonous to them as to other anaerobes. The chemical reaction that occurs when acetogens decompose amino acids is:

$$2C_3H_7NO_3+O_2 \rightarrow 2HC_2H_3O_2+3H_2+N_2+2CO_2$$

serine (amino acid)+oxygen→acetic acid+hydrogen+ nitrogen+carbon dioxide

In some embodiments, the anaerobic digestion system 200 depicted in FIG. 4 performs and accomplishes much of this acidification stage upstream in the blend tank 102 before injecting the feedstock into the digester 100. The feedstock is conditioned for pH and temperature and agitated to promote $CO_2$ release prior to transfer to the digester 100. Note that ammonia can be toxic to the anaerobic digesting process. Ammonium, however, is far more benign and not toxic. Based upon independent and verifiable data, the blend tank 102 combines the ammonia with a free H ($NH_3+H \rightarrow NH_4+$) and converts more than 95% of ammonia to ammonium which is more environmentally benign and less odorous and is concurrent with the hydrolysis stage of anaerobic digestion. Ammonium locks in the nitrogen, preventing a rapid release into the soil, which will burn the plants. Lab results have shown that the effluent (digestate) is nearly free of $NH_3$ and the presence of $NH_4+$ is apparent.

In some embodiments, the anaerobic digestion system 200 depicted in FIG. 4 utilizes blend tank 102 and agitator 108 as a multi-functional apparatus that expedites hydrolysis, acidification and ammonia to ammonium conversion of the feedstock. It provides the means in which the Carbon to Nitrogen ratios can be adjusted as discussed below. It also stabilizes the consistency of the feedstock and brings it to its desired solids percentage in the mixed slurry based upon the consistency measurement sensor within the blend tank recirculation loop.

In some embodiments, the anaerobic digestion system 200 depicted in FIG. 4 sets an optimal range of carbon to nitrogen ratio (C:N, which for a non-limiting example, can be a ratio of 20:1 to 25: during anaerobic digestion. The microbes need nitrogen to multiply, therefore, if the C:N ratio is too high, microbial growth will be inhibited, which assumes limited $N_2$ availability. On the other hand, if the C:N ratio is too low (i.e.—the carbon is too low), then the carbon supply for the methanogens will be insufficient to sustain commercially viable methane production. The microbes combine the acetic acid made by acetogens with hydrogen gas, and carbon dioxide to produce methane gas, water, and carbon dioxide, according to the following equation:

$$HC_2H_3O_2 + 4H_2 + CO_2 \rightarrow 2CH_4 + 2H_2O + CO_2$$

acetic acid+hydrogen gas+carbon dioxide-->methane+water+carbon dioxide

Feedstocks come with a wide variety of C:N ratios. Therefore, the critical need to adjust the C:N ratio in the blend tank 102, prior to the digester in-feed, can be done by blending feedstocks. In the case of a feedstock that is too low in carbon, it can be blended with another feedstock high in nitrogen, to attain an optimal C:N ratio. This pre-treatment practice is done at the blend tank 102 and the blending facilitates the chemical reactions.

In some embodiments, the anaerobic digestion system 200 depicted in FIG. 4 breaks down via blend tank 102 proteins by an enzyme called protease that is secreted by fermentative bacteria. This enzyme separates proteins (polypeptides) into amino acids (peptides). It accomplishes this de-polymerization through the hydrolysis process. In hydrolysis, a water molecule is inserted between the two amino acids that are bonded together. The blend bank 102 breaks the bond between them by capping the free reactive ends with the H and the OH. The protein therefore, is broken down from long chains into its individual molecules, amino acids.

In some embodiments, the blend tank 102 of the anaerobic digestion system 200 depicted in FIG. 4 inoculates the pre-treated feedstock with bacteria at the pre-treatment stage. Anaerobe rich digestate taken from the discharge of the digester infeed valve 130 can be used to inoculate new incoming feedstock at the blend tank 102. The anaerobic digestion process is therefore, "seeded". The amount of digestate required for bacterial inoculation will be independent from the amount of dilution liquid required for the feedstock. Based upon monitored variables, including lab analysis, inoculation may also be accomplished with commercially purchased materials. A booster of enzymes can also be added during this operational phase.

In some embodiments, the blend tank 102 of the anaerobic digestion system 200 depicted in FIG. 4 operates within a percent of total incoming solids, for a non-limiting example, with a range of 0.5% to 20% (by weight). However, in the pre-treatment stage of the process the targeted consistency at the blend tank 102/agitator 108 apparatus will be 2% to 12% to facilitate easier handling and pumping. It is the daily operational decanting of the 3 decanting valves that allow the solids to accumulate to a higher percentage in the digester. Various feedstocks will vary greatly as to their percent of dry solids. Some will have a low percentage of dry solids and thus can be pumped. Other feedstock will have a high percentage of dry solids and therefore need to be conveyed. These solids percentage targets can be adjusted at the blend tank 102/agitator 108 pre-treatment stage. Conditions where percent incoming solids are outside of this range will result in detrimental changes in performance and output.

In some embodiments, the anaerobic digestion system 200 depicted in FIG. 4 removes large inorganic matter from the blend tank 102 via inorganics valve 118 during pretreatment. This operational activity occurs principally at the blend tank 102/agitator 108 apparatus of the pre-treatment phase. Both organic and inorganic matter (such as sand, stones, bolts, screws, etc.) can be removed at this pre-treatment stage. However, the anaerobic digestion system 200 tolerates an acceptable range of inorganic matter within the digester 100.

Digestion

Once the Pre-treatment process is completed, the inoculated feedstock is transferred to the thermophilic anaerobic digester 100 as depicted in FIGS. 1-2, where digestion takes place in a totally enclosed oxygen-free environment, operating within a specific temperature range. The feedstock is conditioned to where the methanogen may be predominant. The thermophilic anaerobic digester 100 can process organic waste within a temperature range of 35° C. to 70° C. to operate optimally. Outside of discussed temperature ranges, the digester performance may be poor when evaluated for volatile solids destruction, methane gas quality and quantity, pathogen reduction and quality of soil amendments.

In some embodiments, the water jacket on the underbelly of the thermophilic anaerobic digester 100 is generally comprised of two zones for temperature management of the digester 100. Such multi-zone configuration heats the vessel contents along the entire digester length, maintaining constant and uniform feedstock/digestate internal temperatures. Quantity of heat zones is based upon application and scale of each usage environment. These zones can be controlled independently, sequentially or together. Two zones 170 are shown on FIG. 4 by way of a non-limiting example. The two heating zones are controlled by independent digester zone one temperature sensor 158 and digester zone two temperature sensor 160, which correspondingly control temperature control valve zone one 152 and temperature control valve zone two 154.

In some embodiments, the thermophilic anaerobic digester 100 of the anaerobic digestion system 200 depicted in FIG. 4 utilizes three decanting valves, top 138A, middle 138B, and bottom 138C, for variable decanting in a digestate and capacity specific manner. The digester 100 allows solids to build up at the top and bottom of the digester by decanting from the middle valve. By selectively drawing digestate from the digester 100 at specific level(s), solids either above (lighter) or below (heavier) than the draw-off level are effectively exposed to the bacteria within the digester 100 for periods greater than the average HRT of the vessels. Therefore, more complete digestion is achieved with corresponding improvements in gas production, gas quality, and volatile solids destruction. Solids build-up (both organic and inorganic) can be decanted from the bottom and upper valves as needed. This in turn allows for channeling of various materials in the feedstock to different outflow streams. This ensures higher and more uniform product quality in the high value product streams such as liquid and solid digestate. The rate of decanting at each of the valves can be adjusted individually to suit the solids content and therefore adjust the SRT of that portion of the product stream.

Post Digestion

In some embodiments, the anaerobic digestion system depicted in FIG. 4 operates as a batch plug flow system. With the addition of controls, the size and frequency of loading the digester 100 can be adjusted such that the digestion process becomes almost continuous based on how it is operated. The processing rate of the digester 100 is determined by the Solids Retention Time (SRT) requirements of the feedstock, which in turn defines the total volatile solids destruction and therefore, the biogas quality and the biogas quantity. In the case of manure, this also defines the percent conversion from ammonia to ammonium. Based on optimizing the process parameters such as the in-feed plug flow volume, consistency, temperature, pH, digester operating temperature, decanting, and agitation can all be controlled by, for a non-limiting example, a programmable logic controller (PLC) system, which can also be used to monitor methane and report methane quantity production levels. However, when necessary, there are manual over-rides that permit operation of the anaerobic digestion system in a manual mode.

In some embodiments, the anaerobic digestion system 200 depicted in FIG. 4 draws off biogas at the gas dome(s) of the digester 100 and piped to a water seal tank 180 to maintain an operating pressure within the digester 100. This internal back pressure is adjustable by varying the liquid level in the water seal tank. This water seal tank 180 is also a safety device, in that it acts as an anti-flashback device or flame arrestor. Explosive or burning gases cannot get past the water seal and back into the digester vessel 42. The biogas bubbles up through this water bath and is subsequently cleaned through the removal of the fine particulate entrained in the biogas. If a further reduction in the biogas moisture content is required coalescing filters are used to condense the entrained water vapor. The biogas flow is then measured for volume and methane content. However, recognizing that various compounds may be collected due to the action of the water trap and may be of value for the utilization of the water trap is essential, considering the fact that the gas is of elevated temperatures adding of water manually may be required.

In some embodiments, the anaerobic digestion system 200 depicted in FIG. 4 further separates and processes the solids and liquids processed and stored in bio mass tank 146 via a solids liquid separator 148, depending on the site conditions (water quality/BOD & COD requirements) and system economics. A required level in the bio mass tank 146 as identified by biomass tank level sensor 140 can trigger the operation of the solids liquid separator 148. The digestate that is transferred from the thermophilic anaerobic digester 100 is transferred by digester discharge pump 134 to the bio mass tank 146 through digestate valve 142 to bio mass tank 146 which in turn is controlled by bio mass tank level sensor 140. The process flow of the anaerobic digestion system 200 generates digestate that is highly suitable for land application as well as a product with a 99.999% pathogen kill. In addition, unlike other processes, the digestion process is virtually complete and no further aerobic (wind-rowing) or secondary anaerobic digestion is required. Based upon marketing requirements of soil amendments, digestate needs only to be further conditioned to achieve specific levels of moisture percentage. A mechanical screw press; membrane; filters and reverse osmosis are methods for this purpose.

Expected variations or differences in the results are contemplated in accordance with the objects and practices of the anaerobic digestion system. It is intended, therefore, that the anaerobic digestion system be defined by the scope of the claims which follow and that such claims be interpreted as broadly as is reasonable.

The invention claimed is:

1. An anaerobic digestion system, comprising:
   a blend tank operable to control and perform pre-treatment of feedstock;
   an anaerobic digester operable to digest the feedstock provided from the blend tank in a totally enclosed oxygen-free environment within a specific temperature range, wherein water jacket on the underbelly of the anaerobic digester is comprised of multiple zones for temperature management of the digester;
   a bio mass tank operable to process liquid digestate from the anaerobic digester.

2. The anaerobic digestion system of claim 1, wherein:
   the anaerobic digestion system operates with a multiplicity of feedstock materials.

3. The anaerobic digestion system of claim 1, wherein:
   the anaerobic digestion system draws a specific volume of digestate from the digester and re-circulates it to the blend tank.

4. The anaerobic digestion system of claim 1, further comprising:
   a pH adjust chemical metering pump and pH sensor operate to adjust pH of the feedstock by chemical injection during recirculation.

5. The anaerobic digestion system of claim 1, further comprising:
   an agitator operable to gently blend and maintain uniform temperature of the feedstock in the blend tank.

6. The anaerobic digestion system of claim 1, wherein:
   the blend tank and the agitator expedite hydrolysis, acidification and ammonia to ammonium conversion of the feedstock as a multi-functional apparatus.

7. The anaerobic digestion system of claim 1, further comprising:
   a heat exchanger and a temperature sensor operable to bring up the feedstock in the blend tank to processing temperatures required in the downstream digester.

8. The anaerobic digestion system of claim 1, wherein:
   the blend tank performs and accomplishes acidification upstream before injecting the feedstock into the digester.

9. The anaerobic digestion system of claim 1, wherein:
   the blend tank assists in the conversion over 95% of ammonia to ammonium.

10. The anaerobic digestion system of claim 1, wherein:
    the blend tank breaks down proteins by an enzyme called protease that is secreted by fermentative bacteria.

11. The anaerobic digestion system of claim 1, wherein:
    the blend tank inoculates the pre-treated feedstock with bacteria at pre-treatment stage using anaerobe digestate taken from the discharge of the digester.

12. The anaerobic digestion system of claim 1, wherein:
    the blend tank operates at a selected total solids which is adjustable and selectable to optimize volatile organic solids reduction.

13. The digester of claim 1, further comprising:
    an inorganics valve operable to remove large inorganic matter from the blend tank during pretreatment.

14. The anaerobic digestion system of claim 1, wherein:
    the feedstock is conditioned in the anaerobic digester to where methanogen is predominant.

15. The anaerobic digestion system of claim 1, wherein:
    the anaerobic digester processes organic waste within a temperature range of 35° C. to 70° C. to operate optimally.

16. The anaerobic digestion system of claim 1, wherein:
the anaerobic digester utilizes multiple decanting valves for variable decanting in a digestate and capacity specific manner.

17. The anaerobic digestion system of claim 1, further comprising:
a programmable logic controller (PLC) system operable to optimize and control one or more of in-feed plug flow volume, consistency, temperature, pH, digester operating temperature, decanting, and agitation of the system.

18. The anaerobic digestion system of claim 1, further comprising:
a chopper pump operable to aggressively blend and bring about homogeneity of particle size of the feedstock in the blend tank and mix and recirculate the material within the blend tank as well as transfer the prepared feedstock downstream to the digester.

19. An anaerobic digestion system, comprising:
a blend tank operable to control and perform pre-treatment of feedstock;
an anaerobic digester operable to digest the feedstock provided from the blend tank in a totally enclosed oxygen-free environment within a specific temperature range;
a bio mass tank operable to process liquid digestate from the anaerobic digester;
a water seal tank operable to draw off biogas to maintain an operating pressure within the digester and filter particulate within the discharge gas stream for feedstock material recovery as well as gas cleaning.

20. The anaerobic digestion system of claim 1, further comprising:
a solids liquid separator operable to separate and process solids and liquids stored in the bio mass tank.

21. An anaerobic digestion system of, comprising:
a blend tank operable to control and perform pre-treatment of feedstock;
an anaerobic digester operable to digest the feedstock provided from the blend tank in a totally enclosed oxygen-free environment within a specific temperature range;
a bio mass tank operable to process liquid digestate from the anaerobic digester;
a consistency measurement sensor operable to measure and control consistency to a specific target consistency of the material prepared in the blend tank prior to transfer to the digester of the feedstock.

22. The anaerobic digestion system of claim 21, wherein:
the consistency measurement sensor controls the consistency of the feedstock in such a way that plug flow integrity of feedstock material is maintained in the digester to ensure no short circuiting of the material and therefore all material is subject to the same HRT and SRT.

23. The anaerobic digestion system of claim 22, wherein:
each plug in the plug flow of the feedstock material is subjected to a number of either thermophilic or mesophilic temperature zones as the plug travels the length of the digester in a customized environment for the feedstock in the digester.

* * * * *